US00PP27057P3

(12) United States Plant Patent
Fisher

(10) Patent No.: US PP27,057 P3
(45) Date of Patent: Aug. 9, 2016

(54) ***SALVIA* PLANT NAMED 'SER-WISH'**

(50) Latin Name: ***Salvia* hybrid**
Varietal Denomination: SER-WISH

(71) Applicant: John Fisher, Orange (AU)

(72) Inventor: John Fisher, Orange (AU)

( * ) Notice: Subject to any disclaimer, the term of this patent is extended or adjusted under 35 U.S.C. 154(b) by 228 days.

(21) Appl. No.: 13/999,016

(22) Filed: Dec. 31, 2013

(65) Prior Publication Data

US 2015/0189822 P1 Jul. 2, 2015

(51) Int. Cl.
*A01H 5/02* (2006.01)

(52) U.S. Cl.
USPC ..... Plt./475

(58) Field of Classification Search
USPC ..... Plt./263.1, 475
See application file for complete search history.

(56) References Cited

PUBLICATIONS

Plantarium: *Salvia* 'SERENDIP6' (Love and Wishes). http://plantarium.nl/en/novelty/salvia-serendip6-love-and-wishes/.*
PLUTO: Plant Variety Database, Oct. 9, 2015, citation for 'SER-WISH'—Austraila (AU).*
PLUTO: Plant Variety Database, Oct. 9, 2015, citation for 'SER-WISH'—New Zealand (NZ).*
PLUTO: Plant Variety Database, Oct. 9, 2015, citation for 'SERDIP6'—European Community (QZ).*

* cited by examiner

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Salvia* hybrid cultivar named 'SER-WISH' is disclosed, characterized by unique bright red-purple to purple flowers and a dark purple calyx color. Plants are upright, dense and have a long flowering season. The new variety is a *Salvia*, typically produced as an outdoor ornamental plant.

3 Drawing Sheets

Latin name of the genus and species: *Salvia* hybrid.
Variety denomination: 'SER-WISH'.

BACKGROUND OF THE INVENTION

The new cultivar is the product of chance discovery. The new variety originated as a naturally occurring whole plant mutation of the commercial variety of *Salvia* hybrid 'Wendy's Wish' U.S. Plant Pat. No. 21,889.

The new variety was discovered by the inventor, John Fisher, a citizen of Australia, during October of 2010 in a commercial greenhouse in Wonga Park, Australia. After identifying the new variety as a potentially interesting selection, the inventor continued confidential testing and propagation of 'SER-WISH' assessing stability of the unique characteristics of this variety.

Asexual reproduction of the new cultivar 'SER-WISH' was first performed at a nursery in Wonga Park, Australia, by vegetative cutting in September of 2011. Access to all plants was restricted, as plants were kept in a location that is not open to the public. Through subsequent propagation by vegetative cuttings, six generations have been reproduced, which have shown that the unique features of this cultivar are stable and reproduced true to type.

SUMMARY OF THE INVENTION

The cultivar 'SER-WISH' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SER-WISH.' These characteristics in combination distinguish 'SER-WISH' as a new and distinct *Salvia* hybrid cultivar:

1. Bright red-purple to purple flower color.
2. Calyx color dark purple.
3. Upright plant habit
4. Dense, compact plant
5. Long flowering season.

PARENT COMPARISON

Plants of the new cultivar 'SER-WISH' are similar to the parent, *Salvia* hybrid 'Wendy's Wish' in most horticultural characteristics. The new variety, however, produces a flower color near Red-Purple 64A and Purple N77A, with a lower lip color near Red-Purple 71B and 71C, the parent variety has a flower color of Red-Purple 64B. Additionally 'SER-WISH' produces different calyx color near Purple N77A and Red-Purple 72B whereas the parent 'Wendy's Wish' produces a calyx near Greyed-Purple 186C.

COMMERCIAL COMPARISON

Plants of the new cultivar 'SER-WISH' can be compared to the commercial variety *Salvia* 'SAL010-1', U.S. Plant Pat. No. 25,183. The new variety, however, produces a flower colored near Red-Purple 64A and Purple N77A, with a lower lip color near Red-Purple 71B and 71C. This comparator produces a flower colored near Red 53C and Red 43B. Calyx of the new variety is colored near Purple N77A and Red- Purple 72B, calyx of this comparator is colored near Greyed-Red group RHS 180 A and 180 B.

BRIEF DESCRIPTION OF THE PHOTOGRAPHS

The accompanying photograph in FIG. 1 illustrates in full color a typical plant of 'SER-WISH' grown in a commercial greenhouse in Wonga Park, Australia. This plant is approximately 6 months old, shown planted in a 20 cm. container.

Figure 1:
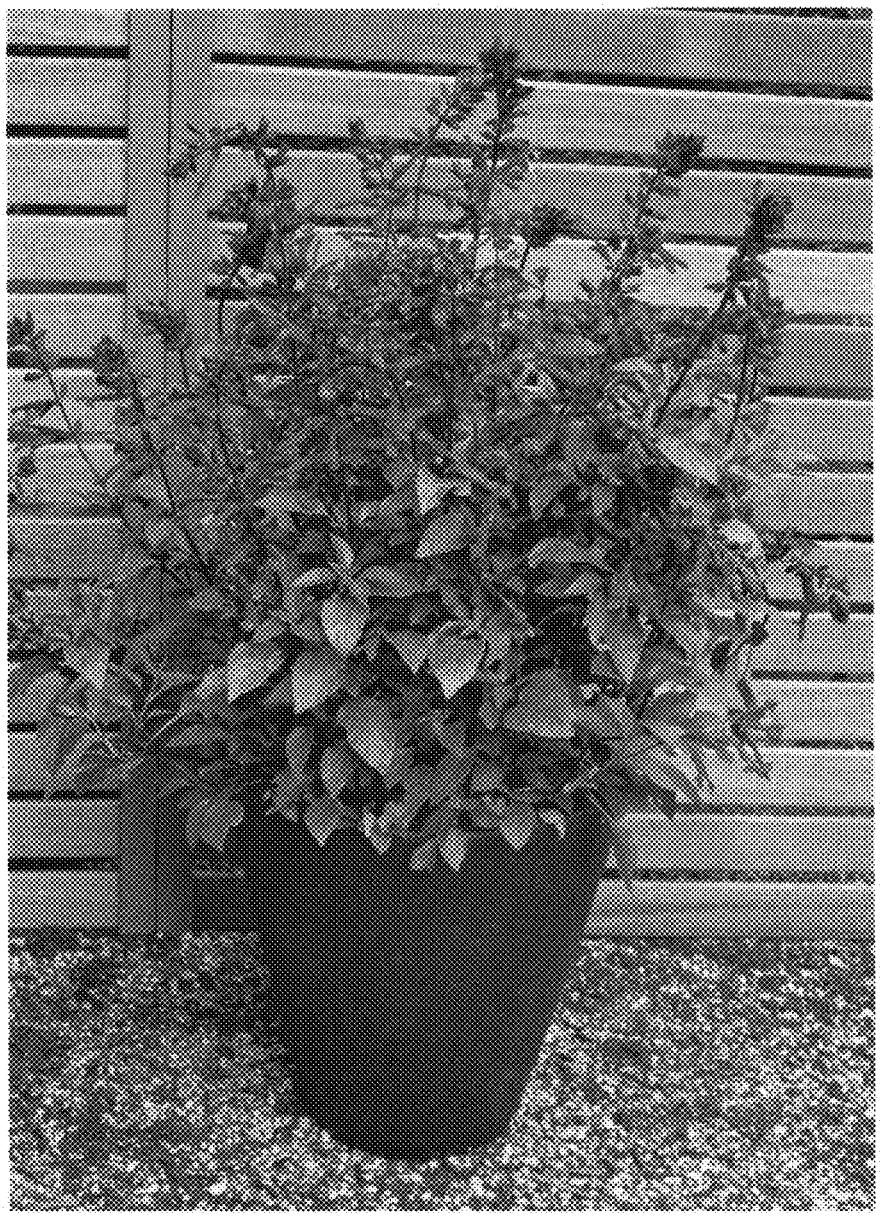
Figure 2:
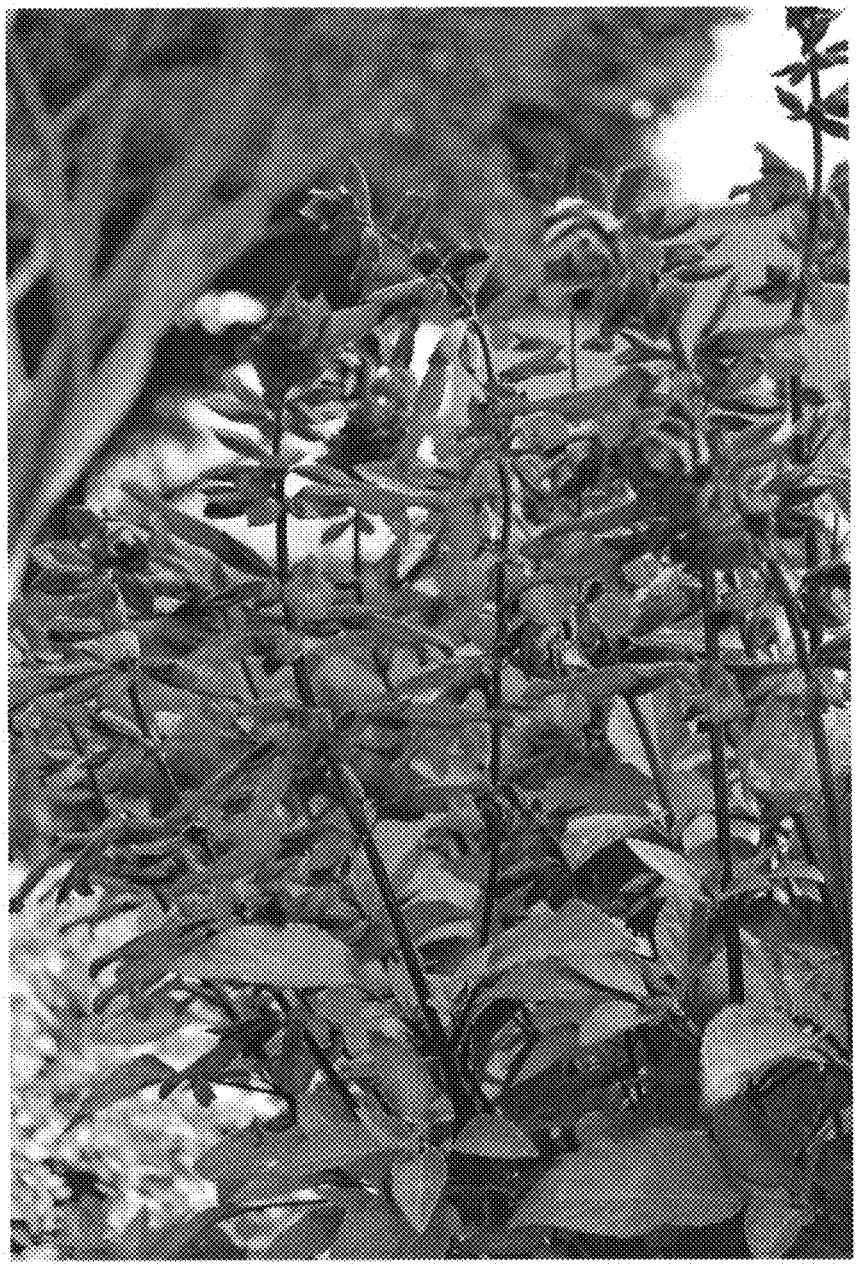
FIG. 2 illustrates in full color a close up of the flowers of 'SER-WISH.
Figure 3:
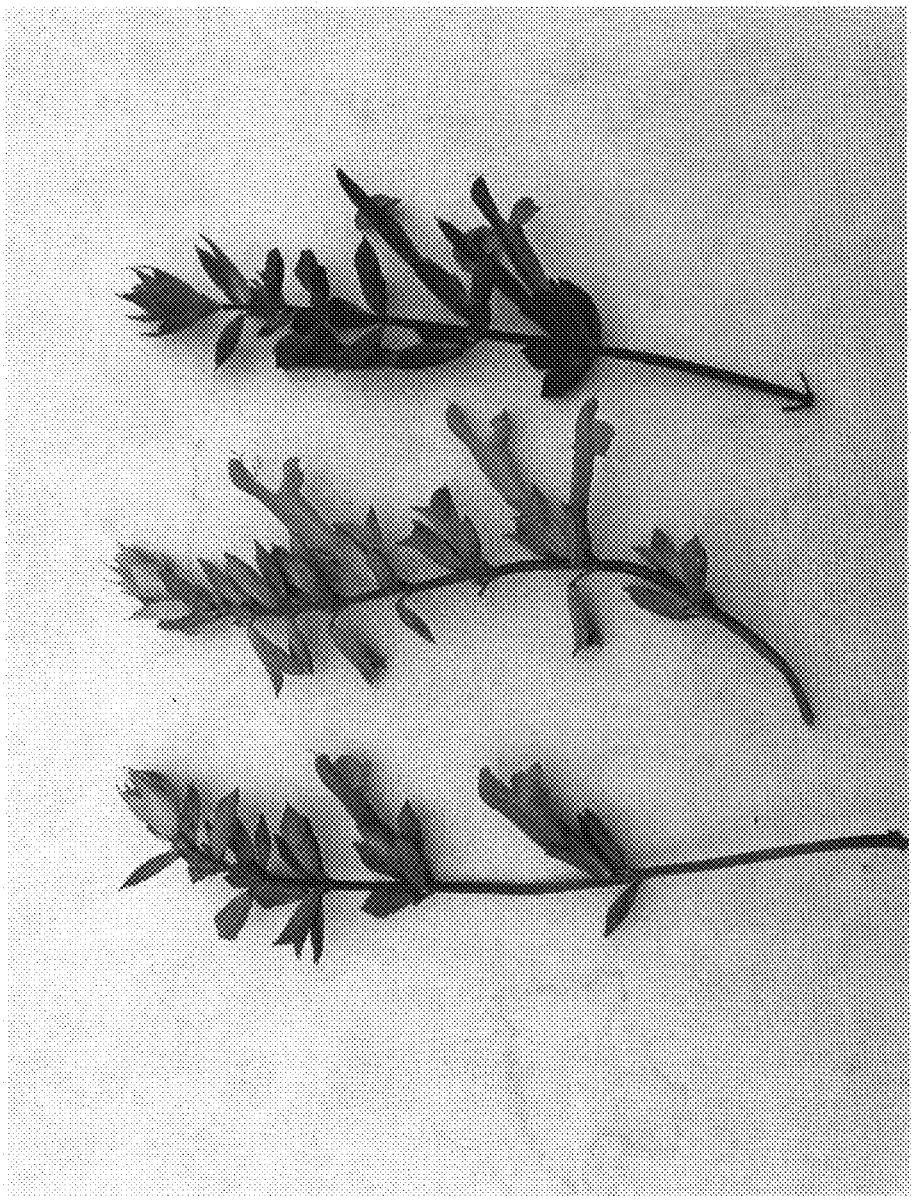
FIG. 3 is a comparison of the following cultivars.

Inflorescence on the right is of the new variety, 'SER-WISH'

Inflorescence in the center is *Salvia* SAL010-1, U.S. Plant Pat. No. 25,183.

Inflorescence on the left is the parent variety 'Wendy's Wish'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'SER-WISH' plants grown outdoors in Camarillo, Calif. Plants are approximately 16 weeks old. Temperatures ranged from 15° C. to 22° C. day and night. No artificial light, photoperiodic treatments were given to the plants. No chemical treatments were given to plants. Measurements and numerical values represent averages of typical plant types. Botanical classification: *Salvia* hybrid 'SER-WISH'.

PROPAGATION

Time to initiate roots: About 10-14 days at approximately 20-21° C.

Time to produce a rooted cutting: About 21-28 days at 20-21° C.

PLANT

Age of plant described: Approximately 16 weeks from a rooted cutting.

Height: Approximately 20 cm.

Plant spread: Approximately 17 cm.

Growth rate: Moderate to fast.

Length of primary lateral branches: Approximately 14 cm.

Diameter of lateral branches: Approximately 0.8 cm.

Quantity of lateral branches: About 6.

Stem:

- *Diameter*.—Approximately 0.8 cm.
- *Color*.—Near Greyed-Purple group RHS N186C.
- *Texture/pubescence*.—Glabrous.
- *Shape*.—Quadrangular.

Internode length: Approximately 3 cm.

FOLIAGE

Leaf:

- *Arrangement*.—Opposite.
- *Quantity*.—Approximately 6 to 10 sets of leaves per main branch.
- *Average length*.—Approximately 4 cm.
- *Average width*.—Approximately 3 cm.
- *Shape of blade*.—Ovate.
- *Apex*.—Acute.
- *Base*.—Cuneate.
- *Attachment*.—Petiolate.
- *Margin*.—Crenate.
- *Texture of top surface*.—Glabrous.
- *Pubescence*.—Absent.
- *Color*.—Young foliage upper side: Near Yellow-Green Group RHS 146B. Young foliage under side: Near Yellow-Green Group RHS 146D. Mature foliage upper side: Near Green Group RHS 137A. Mature foliage under side: Near Yellow-Green Group RHS 147C.
- *Venation*.—Type: Pinnate. Venation color upper side: Near Yellow-Green Group RHS 147C. Venation color under side: Near Greyed-Purple group RHS N186D.
- *Petiole*.—Average Length: Approximately 2.5 cm. Diameter: Approximately 3 mm. Color: Near Greyed-Purple group RHS N187A.

FLOWER

Natural flowering season: Continuously from Mid Spring to Mid Autumn.

Inflorescence type and habit: Raceme.

Flower longevity on plant: Individual flower approximately 4 to 7 days.

Quantity of flowers: About 15 to 20 buds and 3 to 6 fully opened flowers per lateral branch, at one time; or about 10 blooming spikes per plant, for a mature plant of approximately 6 months.

Inflorescence size:

- *Diameter*.—Approximately 4.0 cm.
- *Height*.—Approximately 22.5 cm.

Peduncle:

- *Length*.—7.0 cm.
- *Diameter*.—0.2 cm.
- *Color*.—Near Greyed-Purple group RHS N186B.
- *Orientation*.—Erect.
- *Strength*.—Strong.

Petals:

- *Petal arrangement*.—Fused into a corolla tube, emerging with asymmetrical upper and lower lips.
- *Corolla tube color*.—Near Red-Purple group RHS 64A and Purple N77A.
- *Corolla length*.—4.5 cm.
- *Corolla width*.—1.5 cm. (including lower lip).
- *Corolla tube surface*.—Pubescent.
- *Corolla lip number*.—2.
- *Upper lip shape*.—1 hooded orbicular lip.
- *Upper lip color*.—Near Red-Purple group RHS 64A and Purple N77A.
- *Upper lip surfaces*.—Pubescent.
- *Upper lip length*.—1.3 cm.
- *Upper lip length*.—0.8 cm.
- *Upper lip apex*.—Obtuse.
- *Margin*.—Entire.

*Corolla lower lip shape.*—3 lobed.
*Lower lip base*.—Basally fused.
*Lower lip apex*.—Obtuse.
*Lower lip surfaces*.—Glabrous.
*Corolla lower lip color*.—Upper surface: Near Red-Purple 71B.
*Corolla lower lip color*.—Lower surface: Near Red-Purple 71C.
*Lower lip length.*—1.0 cm.
*Lower lip width.*—1.3 cm.
*Margin*.—Entire.
*Petaloids*.—Not present.

Bud:
*Shape*.—Oblanceolate.
*Length.*—2 cm.
*Diameter.*—0.8 cm.
*Color*.—Near Red-Purple 72B and Purple N77A.
*Texture*.—Pubescent.

Calyx:
*Shape*.—Fused, oblanceolate.
*Length*.—Approximately 2 cm.
*Width*.—Approximately 0.8 cm.
*Texture*.—Pubescent.
*Color*.—Near Purple N77A and Red-Purple 72B.

Sepals:
*Type*.—Fused.
*Apex*.—Acute.
*Margin*.—Entire.
*Texture*.—Pubescent.

Bracts:
*Shape*.—Elliptic.
*Apex*.—Acuminate.
*Margin*.—Entire.
*Color*.—Near Purple N77A.
*Texture*.—Smooth.
*Shape*.—Concave.

REPRODUCTIVE ORGANS

Stamens:
*Number.*—2.
*Filament length*.—Approximately 2 cm.

Anthers:
*Shape*.—Elliptical.
*Length*.—Approximately 3 mm.
*Color*.—Near Greyed-Purple group RHS 186B.
*Pollen*.—Absent.

Pistil:
*Number.*—1.
*Length*.—Approximately 4.5 cm.
*Style*.—Length: Approximately 0.4 cm. Color: Near Red-Purple 59A.
*Stigma*.—Shape: 2 lobed. Color: Near Red-Purple 59A. Ovary color: Near Yellow-Green 153D.

OTHER CHARACTERISTICS

Seeds and fruits: None observed to date.
Disease/pest resistance: Typical for *Salvia*.

What is claimed is:

1. A new and distinct cultivar of *Salvia* hybrid plant named 'SER-WISH' as herein illustrated and described.

* * * * *